United States Patent [19]

Crescentini et al.

[11] Patent Number: 4,582,642
[45] Date of Patent: Apr. 15, 1986

[54] RECOVERY OF CAPROLACTAM FROM PROCESS RESIDUES

[75] Inventors: Lamberto Crescentini; William B. Fisher, both of Chester; Richard E. Mayer, Richmond; Joseph D. DeCaprio, Hopewell; Ronald K. Nilsen, Richmond, all of Va.

[73] Assignee: Allied Corporation, Morris Township, Morris County, N.J.

[21] Appl. No.: 625,143

[22] Filed: Jun. 27, 1984

[51] Int. Cl.$^4$ ............................................. C07D 201/12
[52] U.S. Cl. ................................................ 260/239.3 A
[58] Field of Search ................................. 260/239.3 A

[56] References Cited

U.S. PATENT DOCUMENTS 4,107,160  8/1978  Dicoi ........................... 260/239.3 A
4,148,793  4/1979  Danziger ..................... 260/239.3 A Primary Examiner—Paul R. Michl
Attorney, Agent, or Firm—Richard A. Anderson

[57] ABSTRACT

This invention is a method to recover caprolactam from a combined stream of mother liquor from a caprolactam crystallizer and other lactam containing aqueous streams, the improvement comprising steam distilling the combined stream at a temperature of from between about 180° C. to 235° C. in the absence of any depolymerization agent such as phosphoric acid; so that the residue from the steam distilling remains fluid; relatively low levels of caprolactam remain in the residue; less residue is generated; the recovered caprolactam has improved high quality; and losses of caprolactam due to side reactions are reduced.

2 Claims, 2 Drawing Figures

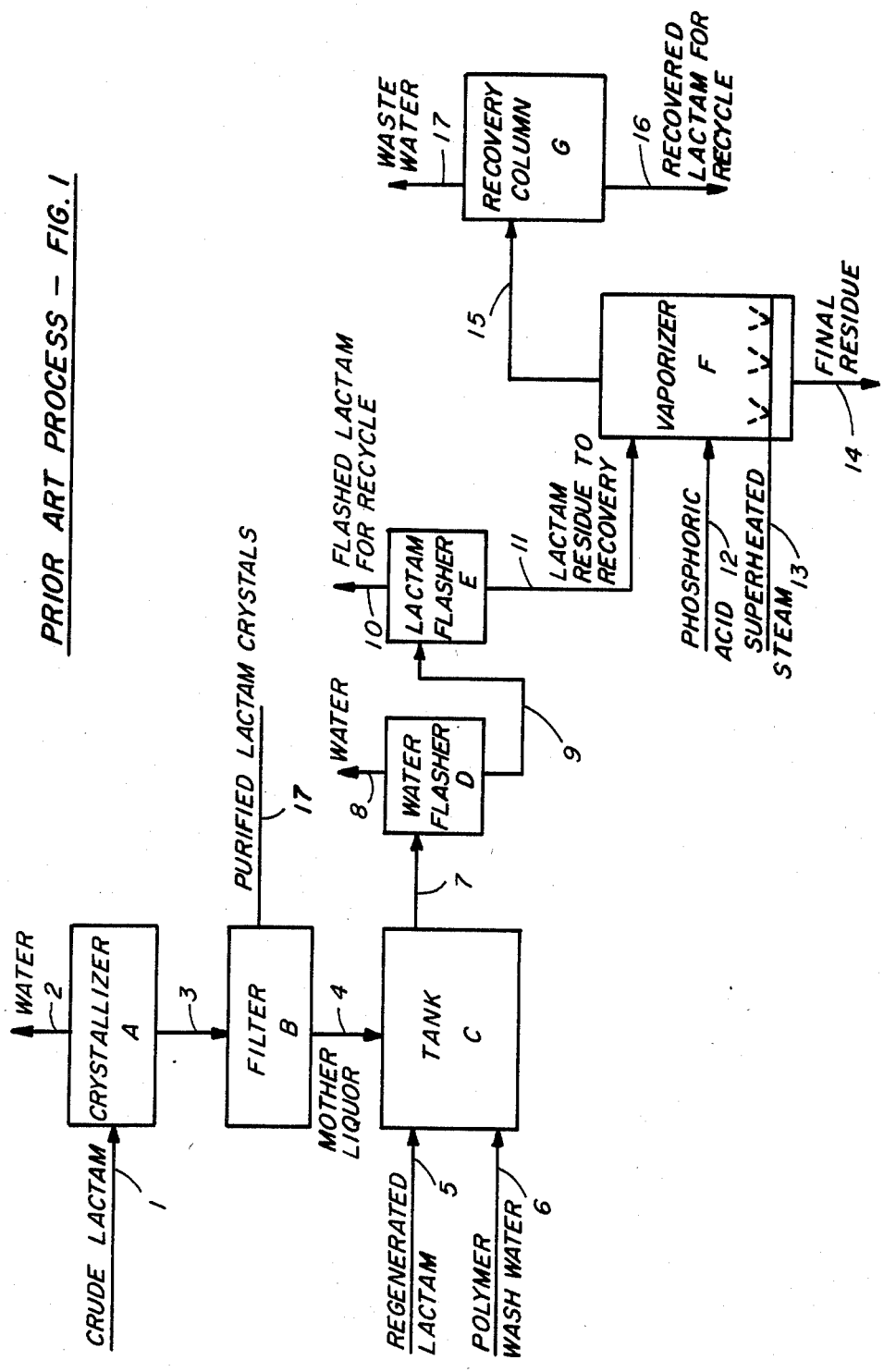

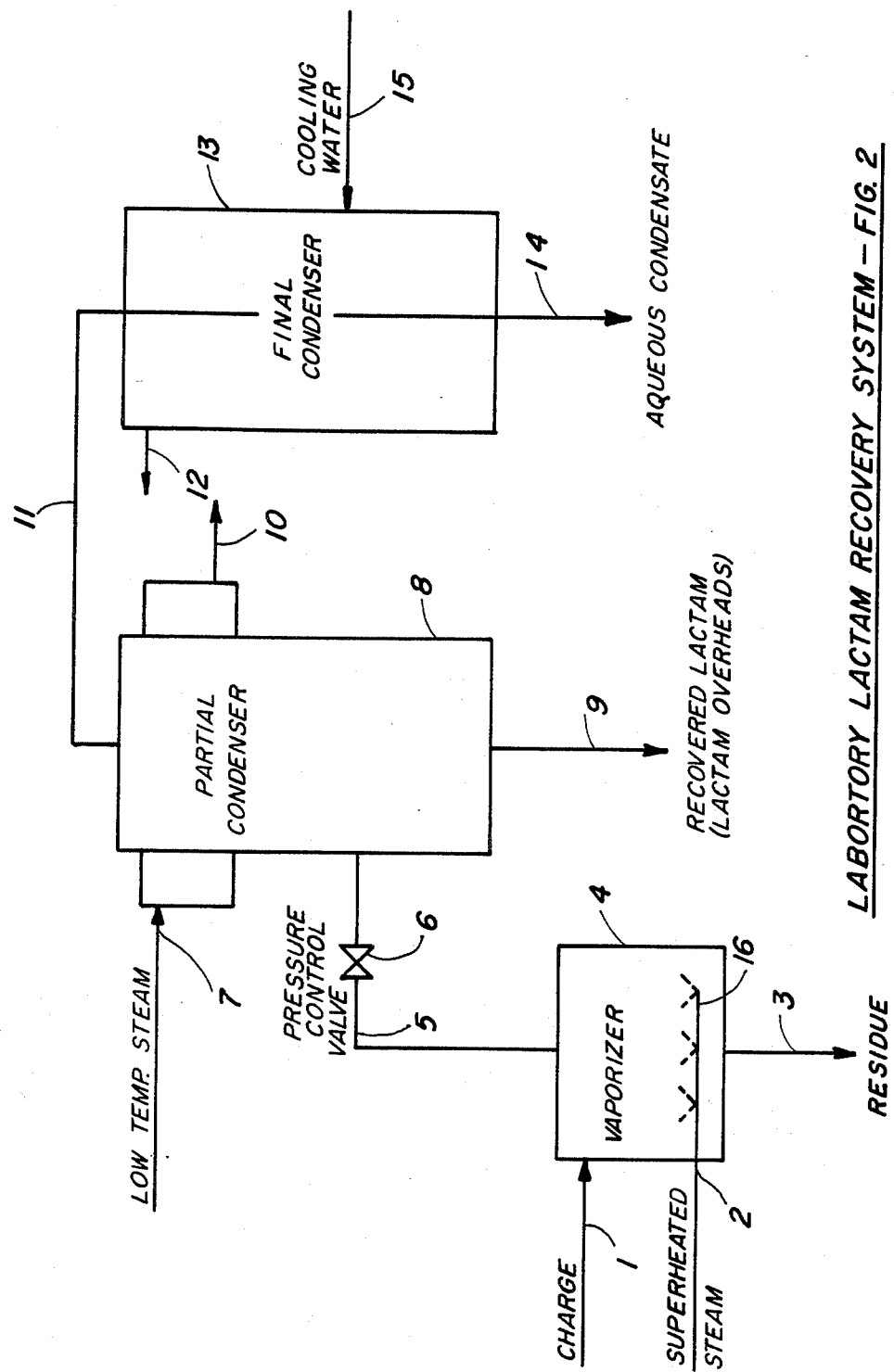

RECOVERY OF CAPROLACTAM FROM PROCESS RESIDUES

BACKGROUND OF THE INVENTION

This invention relates to a method of recovery of caprolactam from process residues by steam distillation. In the prior art process crude epsilon-caprolactam (lactam) is purified by crystallization. Crystals of purified lactam are recovered, and an aqueous mother liquor containing various impurities is separated. To this mother liquor other aqueous streams containing lactam from various sources such as waste fiber depolymerization and polymer washing may be added. Caprolactam is recovered from the combined streams after first vaporizing the water, by flash distillation and a residue is obtained still containing approximately 50% caprolactam.

Since it is uneconomical to discard this lactam, means have been sought and developed over the years for processing this mixture to recover as much lactam as possible. In the prior art process, lactam is removed from this mixture by further vaporization. In order to avoid the high temperatures and complex equipment required to achieve high removal yields in this stage, thus minimize losses of lactam in the residue, maintain adequate residue fluidity, and possibly generate, by depolymerization, lactam for polymeric materials, it has long been the practice to add phosphoric acid, as well as superheated steam in this final vaporization stage. The addition of phosphoric acid has allowed the use of temperatures around 220° C. Under these conditions, it was realized later that little, if any, depolymerization of polymeric material to caprolactam occurs but the fluidity of the vaporization residue is adequate at relatively low levels of residual caprolactam.

SUMMARY OF THE INVENTION

It has now been found, surprisingly, that when the use of phosphoric acid is avoided, lactam can be advantageously recovered from the 50% lactam/residue mixture at the relatively low temperatures of 180°-235° C. by the use of steam alone, that acceptable residue fluidities can still be obtained at relatively low levels of residue caprolactam, that the quality of the caprolactam recovered in the absence of phosphoric acid is improved, that overall losses of lactam due to side reactions are decreased, and that less residue is generated, thus facilitating disposal. In addition, the use of a hazardous material is no longer required as in the prior art.

More specificially, this invention is a method to recover caprolactam from a combined stream of mother liquor from a caprolactam crystallizer and other lactam-containing streams; the improvement comprises steam distilling the combined stream at a temperature of from between about 180° C. and 235° C. in the absence of any depolymerization agent such as phosphoric acid to achieve the above benefits.

BRIEF DESCRIPTION OF THE DRAWINGS

FIG. 1 is a schematic of the process of the prior art.
FIG. 2 is a schematic of the laboratory process of this invention.

DESCRIPTION OF THE PRIOR ART

The prior art process in FIG. 1 consists of crystallizer A, having crude lactam feed line 1, water removal line 2, and exit line 3 for lactam crystals and impurities which pass to filter B which filters impurities and passes purified lactam crystals through line 17 and mother liquor through line 4 to tank C which also receives regenerated lactam through line 5 and polymer wash water through line 6. The combined stream exits through line 7 to water flasher D having overhead line 8 for water and bottoms line 9 to lactam flasher E having overhead line 10 for flashed lactam for recycle and bottoms line 11 to vaporizer F which also receives phosphoric acid through line 12, and superheated steam through line 13. Final residue exits through line 14 and overhead vapors through line 15 to recovery column G where waste water distills overhead through line 17 and recovered lactam exits through bottoms line 16 for recycle.

DESCRIPTION OF THE PREFERRED EMBODIMENTS

The laboratory apparatus of the invention is shown in FIG. 2. Laboratory scale lactam recovery studies were conducted in a 3.6 liter stainless steel vessel 4 which was fitted with a sparge ring 16, a thermocouple to read the internal temperature, an electrically heated vapor exit line 5, and a charge port. The vessel was heated externally with an electric mantle. The material containing lactam was charged to the vessel through line 1. Saturated steam at 40 psia (273 KPa abs) was superheated and metered to the sparge ring at 350° C. through line 2, and the electric heating mantle was adjusted to produce the desired vessel temperature. The contents of the vessel were kept slightly above atmospheric pressure via a control valve 6 in the vapor exit line 5. Residue can be removed from vessel 4 through line 3. Vapors were passed into a 2-foot (60 cm) high vertical partial condenser 8 with steam entering through line 7 and exiting through line 10 at 110°-115° C. in the jacket. The condensate which is high in caprolactam was collected through line 9 in a graduated measuring vessel and is referred to as the lactam overheads.

The vapor exiting the partial condenser through line 11, which is very high in water content, was condensed in a water-cooled condenser 13. It is referred to as the aqueous condensate removed through line 14. Cooling water enters through line 15 and exits through line 12. The steam flow to the sparger was adjusted to produce an aqueous condensate of 750-800 ml/hour. When lactam condensate ceased, the residue was drained by gravity through an opening in the vessel bottom and cooled in a pan. The lactam and aqueous condensates were analyzed for lactam by gas chromatography and for hexenoic acid by ion chromatography. The lactam condensate was analyzed for color and permanganate number (PN). Fluidity of the residue and ease of discharge were also observed. The results of several runs are reported below.

Other than in size, the prior art process differs from the laboratory simulation in the following ways:
(a) the feed is charged continuously, the residue may be discharged continuously or intermittently,
(b) the vapors are fed to a tray column instead of a system of two condensers, and
(c) phosphoric acid is used.

EXAMPLES

COMPARATIVE EXAMPLE
CONTROL WITH H3PO4
LABORATORY RUN

Run Number 1 - Control
Temperature, 235° C.

| | Charge*, Line 1 | Lactam Overheads, Line 9 | Aqueous Condensate, Line 14 | Residue, Line 3 |
|---|---|---|---|---|
| Total Weight of Charge | 2065 | 486 | 3223 | 1290 |
| Phosphoric Acid | 202 | — | — | — |
| Lactam | 814 | 327 | 128 | 56.8 |
| (% of Charge) | 39.4 | 67.3 | 4.0 | 4.4 |
| Oligomers | 254 | — | — | — |
| Hexenoic Acid | 109 | — | — | 33 |
| PN | — | 5400 | — | — |
| Color | — | 6200 | — | — |

% of Charged Lactam Left in Residue, 7.0
% Lactam Recovered, 55.9
% Hexenoic Acid Rejected in Residue, 30.3
% Residue of Charge, 62.5
Fluidity of Residue: Drained Easily
*Taken from line 11 of FIG. 1 process

EXAMPLE 1

Without H3PO4, Better Lactam Recovery, Better Color and Hexenoic Rejection, Less Residue, Residue Has Good Fluidity
Laboratory Run Run Number 2
Temperature, 235° C.

| | Charge*, Line 1 | Lactam Overheads, Line 9 | Aqueous Condensate, Line 14 | Residue, Line 3 |
|---|---|---|---|---|
| Total Weight of Charge | 2672 | 919 | 3417 | 1185 |
| Phosphoric Acid | None | — | — | — |
| Lactam | 1053 | 608 | 181 | 82.9 |
| Oligomers | 329 | — | — | 288 |
| Hexenoic Acid | 141 | — | — | 95.7 |
| PN | — | 5200 | — | — |
| Color | — | 1368 | — | — |

% of Charged Lactam Left in Residue, 7.9
% Lactam Recovered, $\frac{608 + 181}{1053} \times 100 = 74.9$
% Hexenoic Acid Rejected in Residue, 67.9
% Residue of Charge, 44.3
Fluidity of Residue: Drained Easily
*Taken from line 11 of FIG. 1 process

EXAMPLE 2

LOWER TEMPERATURE WITHOUT H3PO4
RESULTS STILL EXCELLENT
LABORATORY RUN

Run Number 3
Temperature, 222° C.

| | Charge*, Line 1 | Lactam Overheads, Line 9 | Aqueous Condensate, Line 14 | Residue, Line 3 |
|---|---|---|---|---|
| Total Weight of Charge | 2640 | 885 | 3527 | 1064 |
| Phosphoric Acid | None | — | — | — |
| Lactam | 1040 | 619 | 176 | 87.2 |
| Oligomers | 325 | — | — | 233 |
| Hexenoic Acid | 140 | — | — | 89.9 |
| PN | — | 4570 | — | — |
| Color | — | 700 | — | — |

% of Charged Lactam Left in Residue, 8.4
% Lactam Recovered, $\frac{619 + 176}{1040} \times 100 = 76.4$
% Hexenoic Acid Rejected in Residue, 64.2
% Residue of Charge, 40.3
Fluidity of Residue: Drained Easily
*Taken from line 11 of FIG. 1 process

EXAMPLE 3

LOWER TEMPERATURE WITHOUT H3PO4
RESULTS STILL EXCELLENT
LABORATORY RUN

Run Number 4
Temperature, 200° C.

| | Charge*, Line 1 | Lactam Overheads, Line 9 | Aqueous Condensate, Line 14 | Residue, Line 3 |
|---|---|---|---|---|
| Total Weight of Charge | 2530 | 946 | 4165 | 1050 |
| Phosphoric Acid | None | — | — | — |
| Lactam | 1340 | 713 | 324 | 166 |
| Oligomers | 359 | — | — | 319 |
| Hexenoic Acid | 112 | — | — | 95.7 |
| PN | — | — | — | — |
| Color | — | — | — | — |

% of Charged Lactam Left in Residue, 12.4
% Lactam Recovered, 77.4
% Hexenoic Acid Rejected in Residue, 85.4
% Residue of Charge, 41.5
Fluidity of Residue: Drained Easily
*Taken from line 11 of FIG. 1 process

EXAMPLE 4

SIMILAR TO RUN NUMBER 4
LABORATORY RUN

Run Number 5
Temperature, 200° C.

| | Charge*, Line 1 | Lactam Overheads, Line 9 | Aqueous Condensate, Line 14 | Residue, Line 3 |
|---|---|---|---|---|
| Total Weight of Charge | 2485 | 858 | 3317 | 1210 |
| Phosphoric Acid | None | — | — | — |
| Lactam | 979 | 583 | 134 | 145 |
| Oligomers | 306 | — | — | 222 |
| Hexenoic Acid | 132 | — | — | 114 |
| PN | — | 3830 | — | — |

-continued

SIMILAR TO RUN NUMBER 4 LABORATORY RUN

Run Number 5
Temperature, 200° C.

Compositions and Properties
Parts by Weight

|  | Charge*, Line 1 | Lactam Over- heads, Line 9 | Aqueous Condensate, Line 14 | Residue, Line 3 |
| --- | --- | --- | --- | --- |
| Color | — | 936 | — | — |

% of Charged Lactam Left in Residue, 14.8
% Lactam Recovered, 73.2
% Hexenoic Acid Rejected in Residue, 86.4
% Residue of Charge, 48.7
Fluidity of Residue: Drained Easily
*Taken from line 11 of FIG. 1 process

EXAMPLE 5

STILL LOWER TEMPERATURE; STILL EXCELLENT RESULTS LABORATORY RUN

Run Number 6
Temperature, 180° C.

Compositions and Properties
Parts by Weight

|  | Charge*, Line 1 | Lactam Over- heads, Line 9 | Aqueous Condensate, Line 14 | Residue, Line 3 |
| --- | --- | --- | --- | --- |
| Total Weight of Charge | 2484 | 905 | 5100 | 1075 |
| Phosphoric Acid | None | — | — | — |
| Lactam | 1292 | 597 | 270 | 158 |
| Oligomers | 353 | — | — | 320 |
| Hexenoic Acid | 109 | — | — | 89.9 |
| PN | — | — | — | — |
| Color | — | — | — | — |

% of Charged Lactam Left in Residue, 12.2
% Lactam Recovered, 67.1
% Hexenoic Acid Rejected in Residue, 82.5
% Residue of Charge, 43.3
Fluidity of Residue: Drained Easily
*Taken from line 11 of FIG. 1 process

EXAMPLE 6

DIFFERENT CHARGE FED TO TREATMENT; EXCELLENT RESULTS LABORATORY RUN

Run Number 7 (Concentrated Mother Liquor)
Temperature, 200° C.

Compositions and Properties
Parts by Weight

|  | Charge*, Line 1 | Lactam Over- heads, Line 9 | Aqueous Condensate, Line 14 | Residue, Line 3 |
| --- | --- | --- | --- | --- |
| Total Weight of Charge | 1040 | 470 | 1720 | 353 |
| Phosphoric Acid | None | — | — | — |
| Lactam | 624 | 400 | 150 | 40 |
| Oligomers | — | — | — | 11.3 |
| Hexenoic Acid | 75.9 | — | — | 52.0 |
| PN | — | — | — | — |
| Color | — | — | — | — |

% of Charged Lactam Left in Residue, 6.4
% Lactam Recovered, 88.1
% Hexenoic Acid Rejected in Residue, 68.5
% Residue of Charge, 33.9
Fluidity of Residue: Drained Easily
*Taken from line 4 of FIG. 1 process with preconcentration by flashing

EXAMPLE 7

STILL DIFFERENT CHARGE FED TO TREATMENT AGAIN, EXCELLENT RESULTS LABORATORY RUN

Run Number 8 (Concentrated Wash Water)
Temperature, 200° C.

Compositions and Properties
Parts by Weight

|  | Charge*, Line 1 | Lactam Over- heads, Line 9 | Aqueous Condensate, Line 14 | Residue, Line 3 |
| --- | --- | --- | --- | --- |
| Total Weight of Charge | 1500 | 701 | 2220 | 530 |
| Phosphoric Acid | None | — | — | — |
| Lactam | 1020 | 568 | 242 | 106 |
| Oligomers | 330 | — | — | 203 |
| Hexenoic Acid | — | — | — | — |
| PN | — | — | — | — |
| Color | — | — | — | — |

% of Charged Lactam Left in Residue, 10.4
% Lactam Recovered, 79.4
% Residue of Charge, 35.3
Fluidity of Residue: Drained Easily
*Taken from line 6 of FIG. 1 process with preconcentration by flashing

DISCUSSION

The values for PN and color were obtained by Allied Standard Test Methods No. 189 (1/67) and No. 230 (4/67) published by Allied Corporation from Morristown, N.J. Hexenoic acid content was determined by ion chromatography. Lactam content was determined by gas chromatography. The PN method is also desribed in U.S. Pat. No. 3 406 167 and U.S. Pat. No. 3 021 326, both hereby incorporated by reference.

We claim:
1. In a method to recover caprolactam from a combined, concentrated stream of mother liquor from a caprolactam crystallizer and other concentrated lactam containing aqueous streams, the improvement comprising
steam distilling said combined stream at a temperature of from between about 180° C. to 235° C. in the absence of any depolymerization agent such as phosphoric acid; so that the residue from said steam distilling remains fluid; relatively low levels of caprolactam remain in said residue; less said residue is generated; the recovered caprolactam has improved high quality; and losses of caprolactam due to side reactions are reduced.
2. In a method to recover caprolactam from a concentrated stream of mother liquor from a caprolactam crystallizer, the improvement comprising
steam distilling said concentrated stream at a temperature of from between about 180° C. to 235° C. in the absence of any depolymerization agent such as phosphoric acid; so that the residue from said steam distilling remains fluid; relatively low levels of caprolactam remain in said residue; less said residue is generated; the recovered caprolactam has improved high quality; and losses of caprolactam due to side reactions are reduced.

* * * * *